United States Patent [19]

Yoshikawa et al.

[11] Patent Number: 5,914,344
[45] Date of Patent: Jun. 22, 1999

[54] SUBSTITUTED CARBOXANILIDE DERIVATIVE AND PLANT DISEASE CONTROL AGENT COMPRISING SAME AS ACTIVE INGREDIENT

[75] Inventors: Yukihiro Yoshikawa; Kanji Tomiya; Naofumi Tomura; Hiroyuki Katsuta; Osamu Takahashi; Shunichi Inami; Yuji Yanase; Junro Kishi; Hideo Kawashima, all of Chiba-ken, Japan

[73] Assignee: Mitsui Chemicals, Inc., Tokyo, Japan

[21] Appl. No.: 08/908,187

[22] Filed: Aug. 7, 1997

[30] Foreign Application Priority Data

Aug. 15, 1996 [JP] Japan ................................. 8-215724
Mar. 13, 1997 [JP] Japan ................................. 9-059106

[51] Int. Cl.$^6$ ........................ A61K 31/415; C07D 231/14
[52] U.S. Cl. ........................ 514/406; 514/363; 514/403; 548/200; 548/202; 548/374.1
[58] Field of Search ..................... 514/363, 403, 514/406; 548/200, 202, 374.1

[56] References Cited

U.S. PATENT DOCUMENTS 5,330,995  7/1994  Eicken et al. ............................ 514/355
5,438,070  8/1995  Eicken et al. ............................ 514/403

FOREIGN PATENT DOCUMENTS 545099  6/1993  European Pat. Off. .
589301  3/1994  European Pat. Off. .

*Primary Examiner*—Yogendra N. Gupta
*Attorney, Agent, or Firm*—Burns, Doane, Swecker & Mathis, L.L.P.

[57] ABSTRACT

A substituted carboxanilide derivative represented by the formula (1):

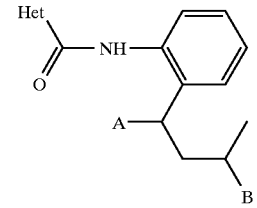

(1)

wherein A is a hydrogen atom or methyl, B is a methyl or ethyl, and Het is 1-methyl-3-substituted-4-pyrazolyl or 2-methyl-4-substituted-5-triazoyl group, exhibits a disease control effect against *Botrytis cinerea*, Powdery mildew, *Pyricularia oryzae* of rice plant and other various plant diseases, is excellent in residual effect, has also activity against resistant strain for conventional chemicals, particularly exerts control effects against *Botrytis cinerea* at a lower dosage as compared with a prior art, is also safe for crops, and thus is useful as a plant control agent.

6 Claims, No Drawings

SUBSTITUTED CARBOXANILIDE DERIVATIVE AND PLANT DISEASE CONTROL AGENT COMPRISING SAME AS ACTIVE INGREDIENT

BACKGROUND OF THE INVENTION

1. Field of the Invention

The present invention relates to a novel substituted carboxanilide derivative and a plant disease control agent comprising the same as an active ingredient.

2. Description of the Related Art

The plant disease control agent which has been developed in recent years and has a selective activity differs from conventionally used, nonselective, plant disease control agent and can exhibit steady effect at a low dosage. However, the plant disease control agent has a problem caused by the development of a resistant fungus leading to a reduction in efficacy.

For example, a benzimidazole-based fungicide has a wide fungicidal spectrum and exhibits excellent effect also on gray mold. However, such fungicide experienced in the 1970's a drastic reduction in efficacy due to appearance of a resistant fungus. A dicarboximide-based fungicide received attention as a replacement for the benzimidazole-based fungicide. Nevertheless, a resistant fungus also appeared in the 1980's against the dicarboximide-based fungicide. Consequently, the counter-measure for controlling the resistant fungus of gray mold has become a serious problem in the world.

On the other hand, an azole-based fungicide has a wide fungicidal spectrum and is an excellent fungicide which exhibits efficacy at a hitherto unexpectedly low dosage particularly for powdery mildew and rust of various crops and scab of apple and pear. However, a resistant fungus against this pesticide has recently appeared and also led to a problem of sharp reduction in the pesticide efficacy. The application number of the fungicide also tends to be limited.

Thus, appearance of the fungicide resistant fungus has become an inevitable problem for the selective plant disease control agent, and accordingly development of a new fungicide is now an urgent subject.

Further, a plant is generally infected by various species of diseases. Representative diseases to be controlled include, for example, blast, sheath blight and other rice diseases, gray mold, powdery mildew and other diseases of cucumber and strawberry; and so as to fruit trees, black spot, scab, rust, powdery mildew and other diseases of pear; and alternaria leaf spot, scab, *Podosphaera leucotricha* and other apple diseases. Even though the generation of these diseases overlaps seasonally, it is generally difficult to control these diseases by single formulation of the fungicide. Accordingly, in recent years, compounds having fungicidal activity are frequently used as a mixture for practical application. As the result, even though the amount of each fungicidally active ingredient in the mixture is small, the total amount of the active compounds to be used generally becomes considerably large. It is assumed in such a case that, when a fungicide which is capable of controlling various species of diseases by single use and is effective even at a low dosage is developed, the field of application will be broad due to excellent efficacy and reduction of adverse effect on the environment.

Several aromatic carboxanilide derivatives have been conventionally known to exhibit fungicidal activity. For example, European Patent A-545099 has recently disclosed that a carboxanilide derivative represented by the formula below has efficacy for *Botrytis cinerea*;

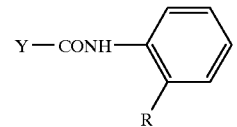

wherein R is an alkyl which has 2–12 carbon atoms and can be halogenated, an alkenyl which has 3–12 carbon atoms and can be halogenated, an alkynyl having 3–6 carbon atoms and can be halogenated, an alkoxy which has 2–12 carbon atoms and can be halogenated, an alkenyloxy which has 3–12 carbon atoms and can be halogenated, an alkynyloxy which has 3–12 carbon atoms, a cycloalkyl which has 3–6 carbon atoms and can be substituted by an alkyl having 1–4 carbon atoms, a cycloalkenyl which has 4–6 carbon atoms and can be substituted by an alkyl having 1–4 carbon atoms, a cycloalkyloxy which has 5–6 carbon atoms and can be substituted by an alkyl having 1–4 carbon atoms, a cycloalkenyloxy which has 5–6 carbon atoms and can be substituted by an alkyl having 1–4 carbon atoms, a phenyl which can be susbstituted by an alkyl having 1–4 carbon atoms, an alkoxy having 1–4 carbon atoms, an alkylthio having 1–4 carbon atoms or halogen, Y is pyridin-3-yl substituted in the 2-position by a halogen, methyl, trifluoromethyl, methoxy, methylthio, methylsulfinyl or methylsulfonyl; phenyl substituted in the 2-position by a methyl, trifluoromethyl, chlorine, bromine or iodine; 2-methyl-5,6-dihydropyran-3-yl, 2-methyl-5,6-dihydro-1,4-oxathiin-3-yl, 2-methyl-5,6-dihydro-1,4-oxathiin-3-yl-4-oxide, 2-methyl-5,6-dihydro-1,4-oxathiin-3-yl-4,4-dioxide; 2-methylfuran-3-yl substituted in the 4- and 5-positions by a hydrogen or methyl; thiazol-5-yl substituted in the 2- and 4-positions by hydrogen, methyl, chlorine or trifluoromethyl; thiazol-4-yl substituted in the 2- and 5-positions by hydrogen, methyl, chlorine or trifluoromethyl; 1-methylpyrazol-4-yl substituted in the 3- and 5-positions by methyl, chlorine or trifluoromethyl; oxazol-5-yl substituted in the 2- and 4-positions by hydrogen, methyl or chlorine.

Further, European Patent A-589301 has disclosed that a carboxanilide derivative represented by the formula below has efficacy for *Botrytis cinerea*;

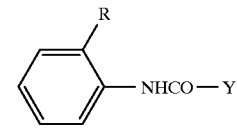

wherein R is an alkyl which has 3–12 carbon atoms and can be partly or completely halogenated, alkoxy having 2–12 carbon atoms, alkenyl having 3–12 carbon atoms, alkenyloxy having 3–12 carbon atoms, alkynyl having 3–6 carbon atoms, alkynyloxy having 3–6 carbon atoms, cycloakyl which has 3–7 carbon atoms and can have one to three alkyls having 1–4 carbon atoms, cycloalkenyl having 4–7 carbon atoms, cycloalkyloxy having 3–7 carbon atoms, cycloalkenyloxy having 4–7 carbon atoms, and phenyl group which can carry one to five halogens and/or one to three of the following radicals; alkyl having 1–4 carbon atoms, haloalkyl having 1–4 carbon atoms, alkoxy having 1–4 carbon atoms, haloalkoxy having 1–4 carbon atoms, alkylthio having 1–4 carbon atoms and haloalkylthio group having 1–4 carbon atoms; and Y is a cyclic group represented by either one of the formulas $Y_1$ to $Y_5$ below:

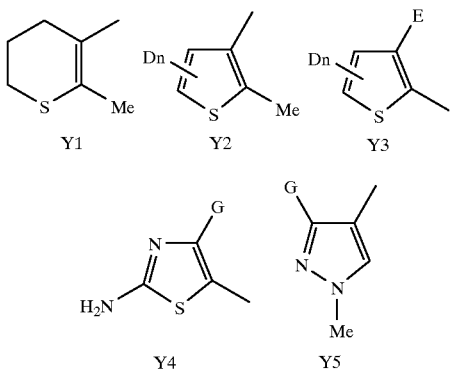

wherein D is a hydrogen atom or alkyl having 1–4 carbon atoms, E is a halogen atom or alkyl having 1–4 carbon atoms, G is an alkyl having 1–4 carbon atoms or haloalkyl having 1–4 carbon atoms, and n is an integer of 1 or 2.

European Patent A-545099 and A-589301 include very broad range of compounds as the highest concept. However, the compounds described in the examples are limited. For example, in the carboxanilide compounds described in these gazettes, the alkyl group which has been specifically described on the examples and tables as a substituent on the 2-position of the aniline ring is restricted to a straight alkyl having 3–7 carbon atoms; isopropyl, sec-butyl, tert-butyl, 1-methylbutyl, 1-methylhexyl and other alkyl groups which are branched at the α-position; and isobutyl, 2-ethylbutyl and other alkyl groups which are branched at the β-position. No description is found at all on the alkyl group which is branched at the γ-position.

The present inventors have tested control activity against various species of plant-pathogenic fungus concerning the specifically disclosed compounds in these gazettes. As a result, neither of the compounds tested had control effect against rice blast. Some compounds had quite no efficacy against Powdery mildew and gray mold. Even though in the case of compounds having efficacy, the effect was very weak.

SUMMARY OF THE INVENTION

Consequently, the object of the invention is to provide a novel substituted carboxanilide derivative having various characteristics of 1) exerting a control effect by single formulation against gray mold, powdery mildew, rice blast and other various diseases, 2) exhibiting efficacy at a low dosage, 3) having an excellent residual effect, 4) having efficacy also for fungi having resistance against existent fungicides, and 5) being safe for crops; a plant disease control agent containing said derivative as an active ingredient; and an intermediate which is useful for preparing said derivative.

The present inventors have been interested in the physiological activity of various carboxanilide derivatives and have conducted research in order to solve the above subjects. As a result, they have found that some of novel carboxanilide derivatives wherein an alkyl group branched at γ-position is located at 2-position on the aniline ring have excellent control effect and residual efficacy against *Botrytis cinerea* and further exhibits an excellent control effect at the same time against Powdery mildew, rice blast and other various diseases. Thus the present invention has been completed.

That is, the aspect of the invention is a substituted carboxanilide derivative represented by the formula (1);

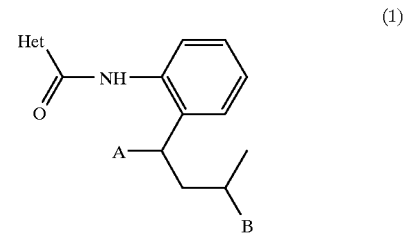

(1)

wherein A is a hydrogen atom or methyl, B is methyl or ethyl, with the proviso that the case wherein A is methyl and B is ethyl group is excluded and Het is a heterocyclic group represented by the formula H1 or H2 below;

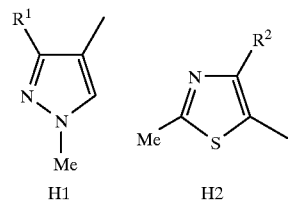

wherein $R^1$ is trifluoromethyl or difluoromethyl, and $R^2$ is trifluoromethyl, difluoromethyl or methyl group, with the proviso that the case wherein A is methyl and B is ethyl group is excluded; a plant disease control agent containing said derivative as an active ingredient; and a substituted aniline derivative which is used as an intermediate for preparing said carboxanilide derivative and is represented by the formula (2) and the formula (3) below;

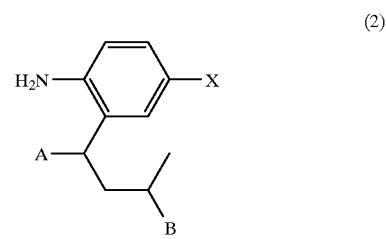

(2)

wherein A is a hydrogen atom or methyl, B is methyl or ethyl, X is a hydrogen atom or halogen atom, with the proviso that the case wherein A is methyl and B is ethyl group is excluded;

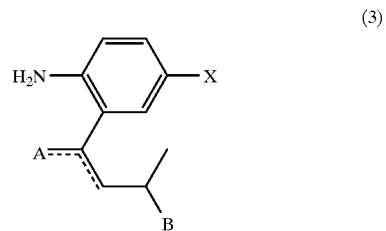

(3)

wherein A is a hydrogen atom or methyl, B is methyl or ethyl, X is a hydrogen atom or halogen atom, dotted lines indicate that either one is a double bond, with the proviso that the case wherein A is methyl and B is ethyl group is excluded.

DETAILED DESCRIPTION OF THE PREFERRED EMBODIMENTS

The compound of the invention is characterized in introducing an alkyl group having a branch at the γ-position into the 2-position on the aniline ring of carboxanilide. The significance of introducing the specific group is very great. The compound of the invention exhibits a control effect and residual effect against gray mold which cannot be inferred from the description in the above gazettes, and also exerts excellent efficacy which could not be conventionally anticipated at all for powdery mildew, rice blast and other various diseases.

In the substituted carboxanilide derivative represented by the formula (1) in the invention, the substituent located on the 2-position of the aniline ring is specifically a 3-methylbutyl, 1,3-dimethylbutyl, 3-methylpentyl and other alkyl groups having a branched structure at the γ-position. The 1,3-dimethylbutyl group is preferred in particular.

The substituents represented by Het are specifically a 1-methyl-3-trifluoromethyl-4-pyrazolyl, 1-methyl-3-difluoromethyl-4-pyrazolyl, 2-methyl-4-trifluoromethyl-5-thiazolyl, 2-methyl-4-difluoromethyl-5-thaizolyl, and 2,4-dimethyl-5-thiazolyl group. Particularly preferred groups are a 1-methyl-3-trifluoromethyl-4-pyrazolyl and 2,4-dimethyl-5-thiazolyl group.

The carboxanilide derivative represented by the formula (1) in the invention can be prepared by the processes (a) to (d) described below.

Process (a)

Substituted aniline represented by the formula (2) is reacted with carbonyl halide represented by the formula (4) in the presence of a base according to the process shown by the reaction formula (1).

Reaction formula (1)

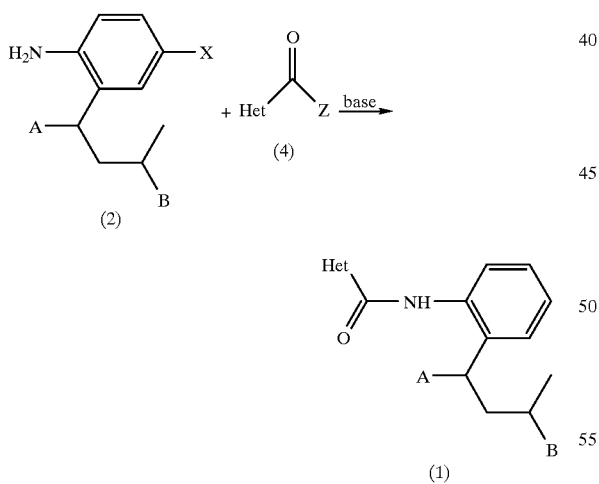

wherein A, B and Het are the same as above, X is a hydrogen atom, and Z is a halogen atom.

Process (b)

Substituted aniline represented by the formula (3) is reacted with carbonyl halide represented by the formula (4) in the presence of a base according to the process shown by the reaction formula (2) to obtain a substituted carboxanilide derivative represented by the formula (5), and successively the double bond is catalytically reduced in the presence of a catalyst, for example, Pd/carbon to prepare the derivative (1).

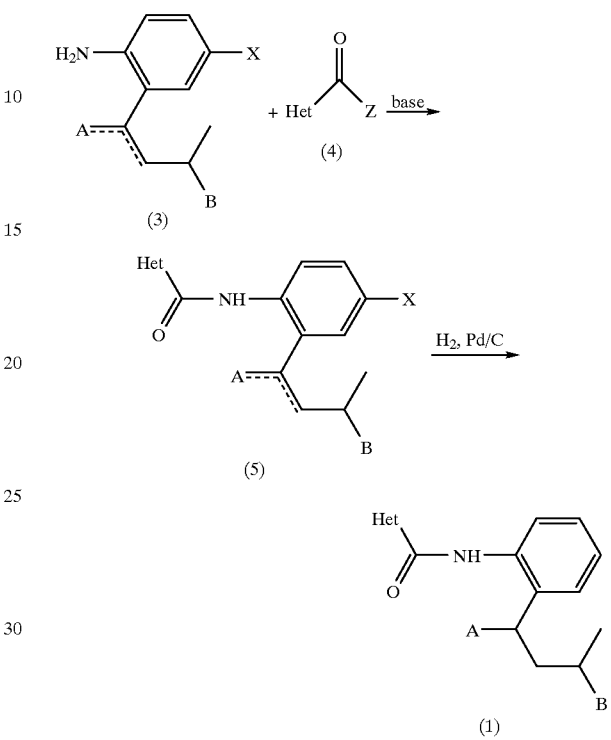

wherein A, B and Het are the same as above, X is a hydrogen atom, Z is a halogen atom, and a dotted line indicates that either one is a double bond.

Process (c)

Substituted aniline represented by the formula (2) is reacted with carbonyl halide represented by the formula (4) in the presence of a base according to the process shown by the reaction formula (3) to obtain a substituted carboxanilide derivative represented by the formula (6) and successively dehalogenated in a hydrogen atmosphere in the presence of a Pd/carbon catalyst and sodium acetate to prepare the derivative (1).

Reaction formula (3)

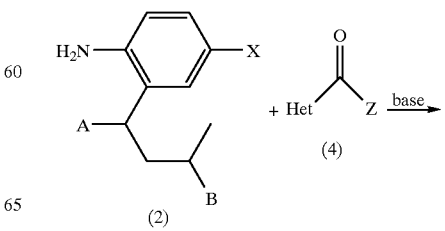

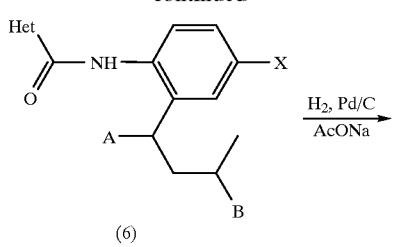

wherein A, B and Het are the same as above, X and Z are halogen atoms and can be same or different.

Process (d)

Substituted aniline represented by the formula (3) is reacted with carbonyl halide represented by the formula (4) in the presence of a base according to the process shown by the reaction formula (4) to obtain a substituted carboxanilide derivative represented by the formula (7), and successively reduction of the double bond and dehalogenation are carried out similarly to the process (c) in a hydrogen atmosphere in the presence of a Pd/carbon catalyst and sodium acetate to prepare the derivative (1).

Reaction formula (4)

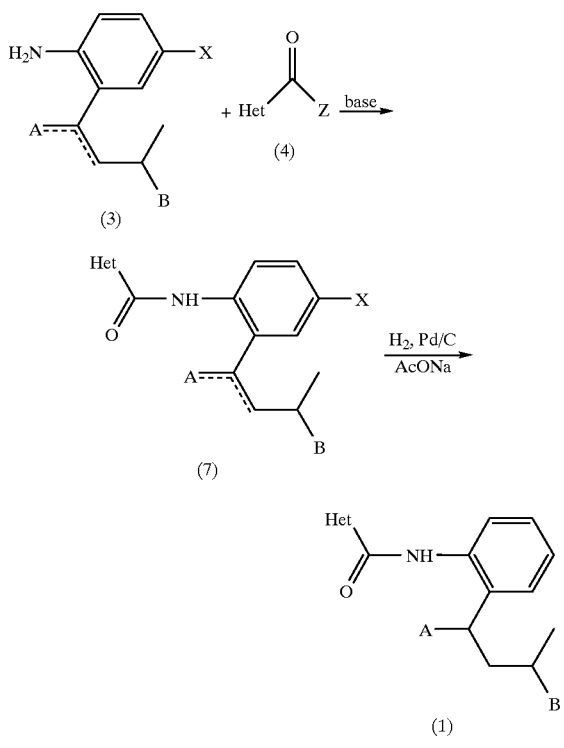

wherein A, B and Het are the same as above, X and Z are a halogen atom and can be the same or different, and a dotted line indicates that either one is a double bond.

Next, these reactions will be illustrated further in detail.

In the carbonyl halide represented by the formula (4), Z is specifically a chlorine, bromine or iodine atom and preferably a chlorine atom.

In the processes (a) to (d), the reaction of substituted aniline represented by the formula (2) or the formula (3) with carbonyl halide represented by the formula (4) can be carried out in the molten state or in a solvent.

The solvents which can be used for the reaction in the invention are inert in the reaction and include, for example, hexane, petroleum ether and other aliphatic hydrocarbons; benzene, toluene, chlorobenzene, anisole and other aromatic compounds; dioxane, tetrahydrofuran, diethyl ether and other ethers; acetonitrile, propionitrile and other nitrile, ethyl acetate and other esters; dichloromethane, chloroform, 1,2-dichloroethane and other halogenated hydrocarbons; and dimethylformamide, dimethylsulfoxide and other aprotic polar solvents. A mixture of these solvents can also be used.

The bases which can be used for the reaction include, for example, sodium hydroxide, potassium hydroxide, calcium hydroxide and other hydroxides of alkali and alkali earth metals; calcium oxide, magnesium oxide and other oxides of alkali and alkali earth metals; sodium hydride, calcium hydride and other hydrides of alkali and alkali earth metals; lithium amide, sodium amide and other amides of alkali metals; sodium carbonate, potassium carbonate, calcium carbonate, magnesium carbonate and other carbonates of alkali and alkali earth metals; sodium hydrogen carbonate, potassium hydrogen carbonate and other hydrogen carbonates of alkali and alkali earth metals; methyllithium, butyllithium, phenyllithium, methylmagnesium chloride and other metal alkyls of alkali and alkali earth metals; sodium methoxide, sodium ethoxide, potassium tert-butoxide, magnesium dimethoxide and other alkoxides of alkali and alkali earth metals; sodium acetate, potassium acetate, magnesium acetate and other carboxylates of alkali and alkali earth metals; and triethylamine, pyridine, N,N-dimethylaniline, N-methylpiperidine, lutidine, 4-dimethylaminopyridine and other various organic bases. Triethylamine and pyridine are preferred in particular. No particular limitation is imposed upon the amount of these bases. These bases are preferably used 5–20 mol % in excess of carbonyl halide represented by the formula (4).

Substituted aniline represented by the above formula (2) or formula (3) is generally used in an amount equimolar with carbonyl halide represented by the formula (4). In some cases, one material is used 1–20% by mole in excess of the other in order to improve yield. The reaction temperature is usually −20–150° C., preferably 0–40° C.

No particular limitation is put upon the reaction time. The reaction time is usually 0.5–5 hours.

No particular restriction is imposed upon the method of reduction in the process (b). A method for reducing a double bond to a single bond [for example, Shin Jikkenkagaku Koza, Vol 15, Oxidation and Reduction, (II), Maruzen (1977)] can be generally applied. However, catalytic reduction is preferred in industry. Reduction catalysts which can be used are metal catalysts which are generally used for catalytic reduction, for example, nickel, palladium, platinum, rhodium, ruthenium, cobalt and copper. A palladium catalyst is preferably used in industry. These catalysts can be used in the state of metal as such. However, these catalysts are commonly used in a supported state on the surface of carriers such as carbon, barium sulfate, silica gel, alumina and Celite. Nickel, cobalt and copper can also be used in the form of a Raney catalyst. A Pd/carbon catalyst which can be applied to catalytic reduction has a Pd-content of 3–20% by weight and is usually used in an amount of 1–30% by weight for the substituted carboxanilide derivative represented by the formula (5).

No particular restriction is imposed upon the reduction method in the processes (c) and (d). The reduction method through removing halogen, for example, Shin Jikkenkagaku Koza, Vol 15, Oxidation and Reduction (II), (1977) can be usually employed. However, preferred methods in industry are catalytic reduction in the presence of a base and hydrazine reduction. The reduction catalysts which can be used are generally the same metallic catalysts as the process (b).

Representative bases which can be used for the reduction include, for example, sodium hydroxide, potassium hydroxide, calcium hydroxide, and other hydroxides of alkali and alkali earth metals; calcium oxide, magnesium oxide and other oxides of alkali and alkali earth metals; sodium hydride, calcium hydride and other hydrides of alkali and alkali earth metals; sodium carbonate, potassium carbonate, calcium carbonate, magnesium carbonate and other carbonates of alkali and alkali earth metals; sodium hydrogen carbonate, potassium hydrogen carbonate and other hydrogen carbonate of alkali and alkali earth metals; sodium methoxide, sodium ethoxide, potassium tert-butoxide, magnesium dimethoxide and other alkoxides of alkali and alkali earth metals; sodium acetate, potassium acetate, magnesium acetate and other carboxylates of alkali and alkali earth metals; aqueous ammonia; and triethylamine, pyridine, N,N-dimethylaniline, N-methylpiperidine, lutidine, 4-dimethylaminopyridine and other various organic bases. Particularly preferred bases are sodium acetate, aqueous ammonia and sodium hydroxide. No particular limitation is put upon the amount of these bases. These bases are preferably used 5–20% by mol in excess of the carboxanilide derivative represented by the formula (6) and formula (7).

Next, the preparation process of the substituted aniline derivatives which are intermediates of the invention and represented by the formula (2) and formula (3) will be illustrated. However, no restriction is imposed upon the preparation process of these substituted aniline derivatives represented by the formula (2) and formula (3).

When X is a hydrogen atom and A is a methyl group in the formula (2) and formula (3), the substituted aniline derivative can be prepared according to the process shown by the reaction formula (5) below.

Reaction formula (5)

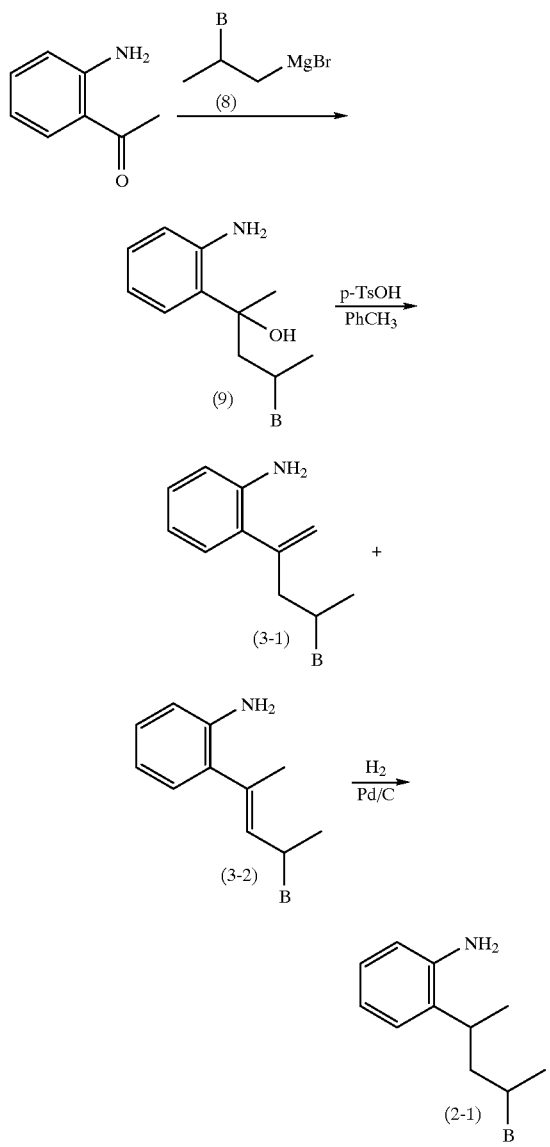

wherein B is the same as above.

That is, 2-aminoacetophenone is reacted with a Grignard reagent of the formula (8) to obtain alcohol of the formula (9), and successively subjected to azeotropic dehydration in toluene in the presence of a catalytic amount of p-toluenesulfonic acid to give alkenes of the formula (3-1) and the formula (3-2). The alkenes are catalytically reduced in the presence of Pd/carbon to prepare the substituted aniline derivative represented by the formula (2-1).

On the other hand, when X is a chlorine atom and A and B are methyl groups in the formula (2), the substituted aniline derivative can be prepared according to the process of G. Bartoli et al. [J. Org. Chem., 45, 522 (1980)] which is shown by the reaction formula (6) below.

Reaction formula (6)

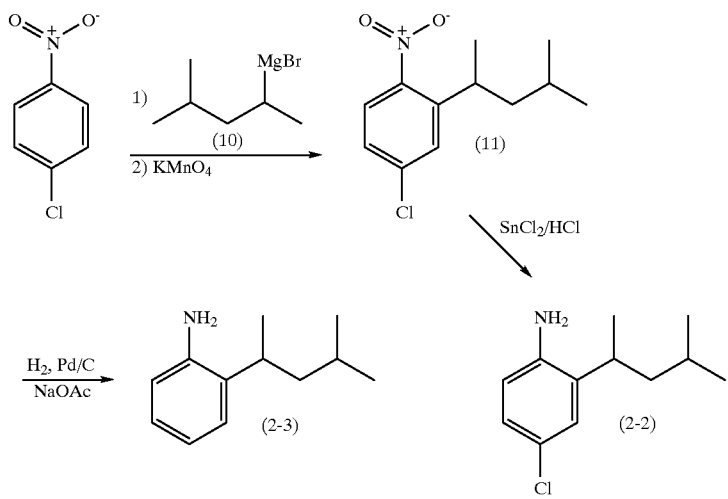

That is, p-chloronitrobenzene is reacted with a Grignard reagent of the formula (10) and successively oxidized with potassium permanganate to obtain the nitro compound of the formula (11). The nitro compound is reduced with stannous chloride and hydrochloric acid to prepare the substituted aniline derivative represented by the formula (2-2). And the nitro compound of the formula (11) is catalytically reduced in the presence of Pd/carbon and sodium acetate to prepare the substituted aniline derivative represented by the formula (2-3).

Further, when X is a chlorine atom and A is a methyl group in the formula (3), the substituted aniline derivative can be prepared according to the process shown by the reaction formula (7) below.

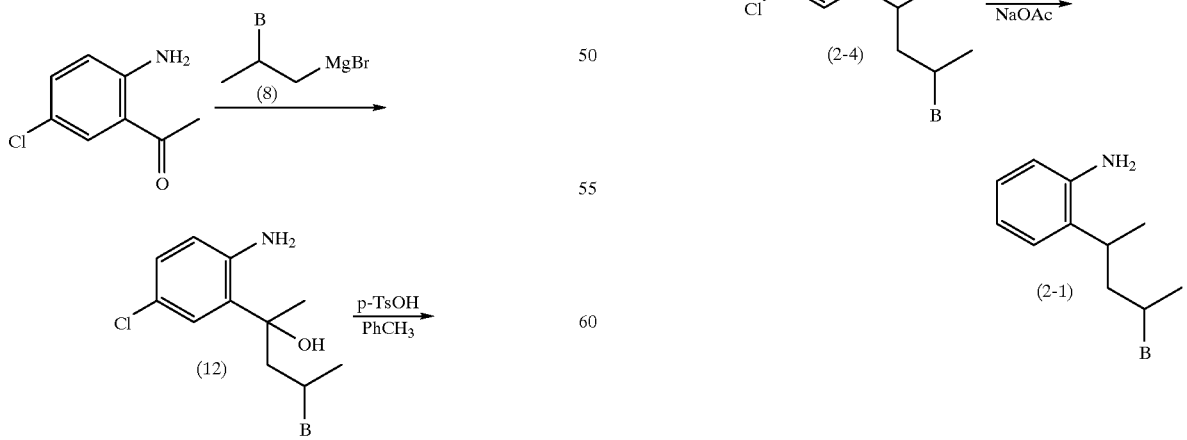

wherein B is the same as above.

That is, 2-amino-5-chloroacetophenone is reacted with a Grignard reagent of the formula (8) to obtain alcohol of the formula (12). Alcohol is subjected to azeotropic dehydration in toluene in the presence of a catalytic amount of p-toluenesulfonic acid to give alkenes of the formula (3-3) and formula (3-4). The double bond alone in alkenes is catalytically reduced in the presence of Pd/carbon to give a substituted aniline derivative of the formula (2-4) which is further catalytically reduced in the presence of a base such as sodium acetate to prepare the substituted aniline derivative represented by the formula (2-1).

Moreover, when A is a hydrogen atom, B is a methyl group, and X is a hydrogen atom or chlorine atom in the formula (2), the substituted aniline derivative can be prepared according to the process shown by the reaction formula (8) below.

Reaction formula (8)

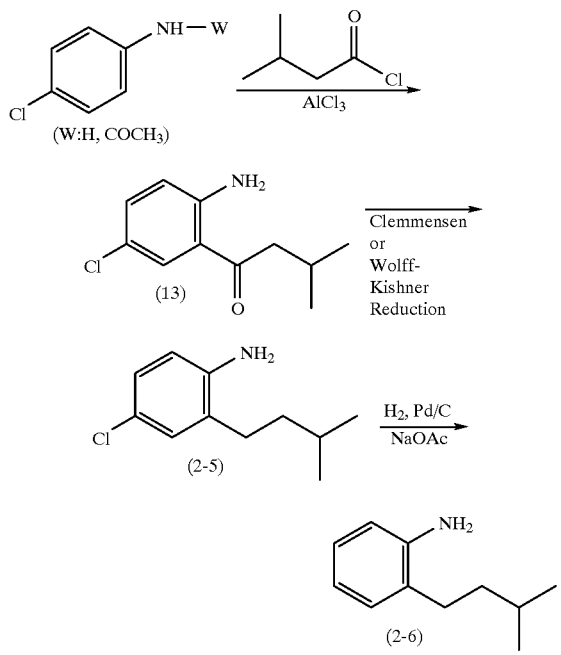

wherein W is a hydrogen atom or an acetyl group.

That is, 4-chloroaniline or the N-acetyl derivative of the same is subjected to a Friedel-Crafts acylating reaction by using 3-methylbutanoyl chloride in the presence of a catalyst such as aluminum chloride to obtain an acylated compound of the formula (13). Successively, the carbonyl group of the acylated compound is subjected to Clemmensen reduction or Wolff-Kishner reduction [for example, Shin Jikkenkagaku Koza, Vol 15, Oxidation and Reduction (II), Maruzen (1977)] to give a substituted aniline derivative of the formula (2-5) which is further catalytically reduced in the presence of a Pd/C catalyst and sodium acetate to prepare the substituted aniline derivative represented by the formula (2-6).

Still more, when A is a hydrogen atom, B is a methyl group, and X is a hydrogen atom in the formula (2), the substituted aniline derivative represented by the formula (2-7) above can also be prepared by nitrating (3-methylbutyl)benzene in a mixture of concentrated nitric acid and concentrated sulfuric acid to obtain a nitro compound of the formula (14) and successively reducing the nitro compound with iron in a concentrated aqueous hydrochloric acid solution as shown in the reaction formula (9) below.

Reaction formula (9)

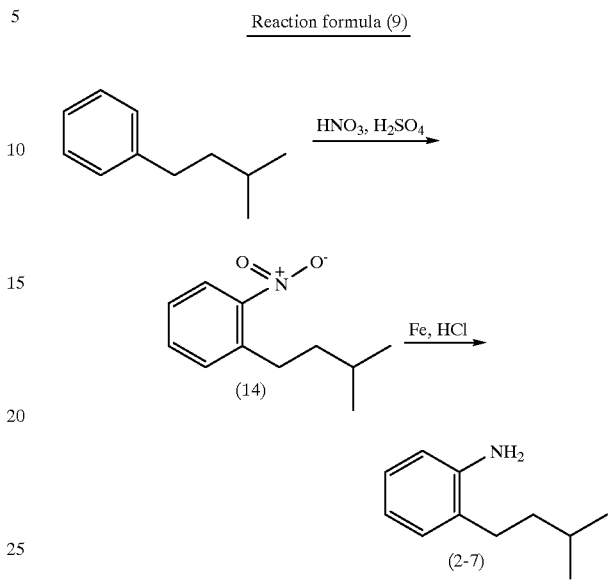

The compound represented by the formula (1) in the invention and the plant disease control agent comprising the same as an active ingredient always exhibit an excellent activity for blast(*Pyricularia oryzae*) of rice, powdery mildew(*Sphaerotheca fuliginea*) of cucurbitaceae, gray mold(*Botrytis cinerea*) of kidney beans, cucumber, tomato, strawberry, grape, potato, soybean, cabbage, Japanese eggplant and lettuce. Moreover, the compound and the plant desease control agent exhibit an activity sheath blight (*Rhizoctonia solani*) of rice, powdery mildew(*Erysiphe graminis* f.sp.*hordei*; f.sp.*tritici*) and stripe rust(*Puccinia striiformis P. graminis; P. recondita; P. hordei*) of wheat, rust(*Phakopsora ampelopsidis*) of grape, scab(*Venturia inaequalis*), alternaria leaf spot(*Alternaria mali*), rust (*Gymnosporang ium yamadae*) and blossom blight (*Sclerotinia mali*) of apple, black spot(*Alternaria kikuchiana*), scab(*Venturia nashicola*) and rust (*Gymnosporangium haraeanum*) of pear, brown rot (*Sclerotinia cinerea*) of peach, rust(*Puccinia allii*) of leek, powdery mildew(*Sphaerotheca humuli*) of strawberry, sclerotinia rot(*Sclerotinia sclerotiorum*) of kidney beans, cucumber, tomato, strawberry, grape, potato, soybean, cabbage, Japanese eggplant and lettuce. That is, the substituted carboxanilide represented by formula (1) in the invention exhibits an efficacy for Botrytis, Sclerotinia, Rhizoctonia, Puccinia, Gymnosporangium, Pyricularia, Sphaerotheca, Alternaria and Venturia.

Other diseases which have possibility of being treated with the compound of the formula (1) of the invention and the plant disease control agent containing the same as an ingredient include helminthosporium leaf spot(*Cochliobolus miyabeanus*) and "Bakanae" disease(*Gibberella fujikuroi*) of rice, leaf stripe(*Pyrenophora graminea*), net blotch (*Pyrenophora teres*), Fusarium blight(*Gibberel la zeae*), snow rot(Typhula sp.; *Micronectriella nivalis*), loose smut (*Ustilago tritici; U. nuda*), eye spot(*Pseudocercosporella herpotrichoides*), rhynchosporium leaf blotch (*Rhynchosporium secalis*), septoria leaf blotch(*Septoria tritici*) and glume blotch(*Leptosphaeria nodorum*) of cereals, powdery mildew(*Uncinula necator*), anthracnose (*Elsinoe ampelina*) and ripe rot(*Glomerella cingulata*) of grape, melanose(*Diporthe citri*) of citrus fruits, powdery mildew(*Podosphaera leucotricha*) and canker(*Valsa mali*) of apple, physalospora canker(*Physalospora piricola*) of pear, scab(*Cladosporium carpophilum*) and phomopsis rot (Phomopsis sp.) of peach, anthracnose(*Gloeosporium kaki*), angular leaf spot(*Cercospora kaki; Mycosphaerella nawae*) and powdery mildew(*Phyllactinia kakikora*) of persimmon, anthracnose(*Colletotrichum lagenarium*) and gummy stem blight(*Mycosphaerella melonis*) of cucurbinaceae, early blight(*Alternaria solani*) and leaf mold(*Cladosporium fulvam*) of tomato, powdery mildew(*Erysiphe cichoracearum*) of Japanese eggplant, alternaria leaf spot (*Alternaria japonica*) and white spot(*Cercosporell a barassicae*) of Brassicaceae, alternaria leaf spot(*Alternaria porri*) of leek, purple speck(*Cercospora kikuchii*), sphaceloma scab(*Elsinoe glycines*) and pod and stem blight (*Diaporthe phaseololum*) of soybean, anthracnose (*Colletotrichum lindemuthianum*) of kidney beans, leaf spot (*Mycosphaerella personatum*) and brown leaf spot (*Cercospora arachidicola*) of peanut, powdery mildew (*Erysiphe pisi*) of pea, early blight(*Alternaria solani*) and black scurf(*Rhizoctonia solani*) of potato, net blister blight (*Exobasidium reticulatum*), white scab(*Elsinoe leucospila*) and anthracnose(*Collet otrichum theae-sinensis*) of tea, brown spot(*Alternaria longipes*), powdery mildew(*Erysiphe cichoracearum*) and anthracnose(*Colletotrichum tabacum*) of tobacco plant, cercospora leaf spot(*Cercospora beticola*) of beet, black spot(*Diplocarpon rosae*) and powdery mildew (*Sphaerotheca pannosa*) of rose, leaf blotch(*Septoria chrysanthemi-indici*) and rust(*Puccinia horiana*) of chrysanthemum, white spot(*Cercosporella brassicae*) of Chinese cabbage, and leaf blight(*Alternaria dauci*) of carrot.

When the compound represented by the formula (1) in the invention is used as a plant disease control agent, the technical product can be used as intact for the plant to be treated. However, the technical product is generally mixed with an inert liquid or solid carrier and used in the form of a dust, wettable powder, flowable formulation, emulsifiable concentrate, granule and other commonly applied formulations. Further, adjuvants can be also added, when necessary.

The term referred to as "carrier" hereupon means a synthetic or natural, inorganic or organic material which is formulated in order to assist application of the active ingredient to the site to be treated and to make storage, transportation and handling of the active ingredient. Both solid and liquid carriers can be used so long as the carriers are commonly used for agricultural and horticultural chemicals. No particular restriction is imposed upon the carriers.

Exemplary solid carriers which can be used include, for example, montmorillonite, kaolinite and other species of clay, diatomaceous earth, clay, talc, vermiculite, gypsum, calcium carbonate, silica gel, ammonium sulfate and other inorganic materials; and soybean flour, saw dust, wheat flour and other plant organic matters and urea.

Representative liquid carriers include, for example, toluene, xylene, cumene and other aromatic hydrocarbons; kerosene, mineral oil and other paraffin hydrocarbons; acetone, methyl ethyl ketone and other ketones; dioxane, diethyleneglycol dimethyl ether and other ethers; methanol, ethanol, propanol, ethylene glycol and other alcohols; and dimethylformamide, dimethyl sulfoxide and other aprotic polar solvents and water.

Further, in order to enhance activity of the compound of the invention, following adjuvants can be also used singly or in combination depending upon the object in view of the formulation and application place.

Adjuvants which can be added are surface active agents which are commonly used for agricultural and horticultural chemicals; binders such as lignin sulfonic acid, alginic acid, polyvinyl alcohol, gum arabic and CMC-sodium; stabilizers such as phenolic compounds, thiol compounds, higher fatty acid esters and other antioxidants; phosphates as pH controllers; and light stabilizers. These adjuvants can be used, when necessary, singly or as a mixture. Further, in order to prevent the plant from bacteria and fungus, a bactericide or industrial fungicide can also be added.

The adjuvants will hereinafter be illustrated further in detail.

Exemplary adjuvants which can be used for purpose of emulsification, dispersion, spreading, wetting, binding and stabilization include lignin sulfonate, alkylbenzene sulfonate, alkylsulfate ester salt, polyoxalkylene alkylsulfate, polyoxyalkylene alkylphosphate ester salt and other anionic surface active agents; polyoxyalkylene alkyl ether, polyoxyalkylene alkyl aryl ether, polyoxyalkylene alkylamine, polyoxyalkylene alkylamide, polyoxyalkylene alkylthioether, polyoxyalkylene fatty acid ester, glycerol fatty acid ester, sorbitan fatty acid ester, polyoxyalkylene sorbitan fatty acid ester, polyoxypropylene polyoxyethylene block copolymer, and other nonionic surface active agents; calcium stearate, wax and other lubricants; isopropyl hydrogen phosphate and other stabilizers; and other materials such as methylcellulose, carboxymethylcellulose, casein and gum arabic. However, no restriction is imposed upon these adjuvants.

The content of the compound represented by the formula (1) in the plant disease control agent of the invention differs depending upon the type of formulation, and is usually 0.05–20 wt % in dust, 0.1–80 wt % in wettable powder, 0.1–20 wt % in granule, 1–50 wt % in emulsifiable concentrate, 1–50 wt % in flowable formulation, and 1–80 wt % in dry flowable formulation, preferably 0.5–5 wt % in dust, 5–80 wt % in wettable powder, 0.5–8 wt % in granule, 5–20 wt % in emulsifiable concentrate, 5–50 wt % in flowable formulation, and 5–50 wt % in dry flowable formulation.

The content of adjuvants is 0–80 wt % and the content of the carrier is an amount obtained by subtracting the contents of the active ingredient and adjuvant from 100 wt %.

The application methods of the plant disease control agent of the invention include seed disinfection and foliage application. Satisfactory activity can be obtained by any method which is usually employed by those skilled in the art. The amount and concentration in applying the agent vary depending upon object crops, object diseases, level of disease development, formulation of the compound, application method and various kinds of environmental conditions. In the case of spray, the amount of active ingredients is suitably 50–1,000 g/ha, desirably 100–500 g/ha. When the wettable powder, flowable formulation or emulsifiable concentrate is sprayed after diluting with water, the dilution is suitably 200–20,000 times, desirably 1,000–5,000 times.

The plant disease control agent of the invention can of course be used as a mixture with other fungicides, insecticides, herbicide, plant growth regulators and other agricultural chemicals, soil conditioners or materials having fertilizer effect and additionally, can be applied with these chemicals in the form of one formulation.

Fungicides which can be used include, for example, triadimefon, hexaconazole, prochloraz, triflumizole and other azole-based fungicides; metalaxyl, oxadixyl and other acyl alanine-based fungicides; thiophanate-methyl, benomil and other benzimidazole-based fungicides; manzeb and other dithiocarbamate-based fungicides; and TPN and sulphur.

Insecticides which can be used include, for example, fenitrothion, diazinon, pyridafenthion, chloropyrifos, marathon, phenthoate, dimethoate, methyl thiometon, protihofos, DDVP, p-acephate, salithion, EPN, and other organophosphate-based insecticides; NAC, MTMC, BPMC, pirimicarb, carbosulfan, methomyl, and other carbonate-based insecticides; and ethofenprox, permethrin fenvalerate and other pyrethroide-based insecticides. However, no restriction is imposed upon these agricultural chemicals.

EXAMPLE

The compound of the invention will hereinafter be illustrated further in detail by way of examples.

Example 1

Preparation of N-[2-(1,3-dimethylbutyl)phenyl]-2,4-dimethylthiazole-5-carboxamide (Compound No. 7)

(1) Process (a): direct process

To a solution containing 0.43 g (2.45 mmol) of 2-(1,3-dimethylbutyl) aniline in 2 ml of pyridine, 0.47 g (2.7 mmol) of 2,4-dimethylthiazole-5-carbonyl chloride was added dropwise with stirring at room temperature.

After stirring for 1 hour, the reaction mixture was poured into 5% aqueous hydrochloric acid solution and extracted with ethyl acetate. The organic layer was washed successively with a saturated aqueous sodium hydrogen carbonate solution and a saturated aqueous sodium chloride solution, and dried over anhydrous sodium sulfate. After distilling off the solvent under reduced pressure, the residue was purified by silica gel column chromatography using a mixture: n-hexane/ethyl acetate=1:1 as an eluent and crystallized from hexane to obtain 0.58 g of the desired product as a colorless crystal. Yield was 75%. Melting point was 130.5° C. (dec.)

$^1$NMR(270 MHz, CDCl$_3$, δ ppm):0.86(6H, d, J=4.4 Hz), 1.23(3H, d, J=6.6 Hz), 1.40–1.53(3H, m), 2.72(3H, s), 2.73(3H, s), 2.96(1H, m), 7.21–7.30(4H, m), 7.70(1H, brs)

Example 2

Preparation of N-[2-(1,3-dimethylbutyl)phenyl]-3-trifluoromethyl-1-methylpyrazole-4-carboxamide (Compound No. 1)

(1) Process (a): direct process

To a solution containing 0.23 g (1.30 mmol) of 2-(1,3-dimethylbutyl) aniline in 2 ml of pyridine, 0.28 g (1.32 mmol) of 3-trifluoromethyl-1-methyl-4-pyrazolecarbonyl chloride was added dropwise with stirring at the room temperature.

After stirring for 1 hour, the reaction mixture was poured into a 5% aqueous hydrochloric acid solution and extracted with ethyl acetate. The organic layer was washed successively with a saturated aqueous sodium hydrogen carbonate solution and a saturated aqueous sodium chloride solution and dried over anhydrous sodium sulfate. After distilling off the solvent under reduced pressure, the residue was purified by silica gel column chromatography using a mixture: n-hexane/ethyl acetate=1:1 as an eluent and crystallized from hexane. The desired product thus obtained was 0.32 g. Yield was 73%. The product was a colorless crystal and had a melting point of 111–113° C.

$^1$NMR(270 MHz, CDCl$_3$, δ ppm):0.82(6H, d, J=4.9 Hz), 1.18(3H, d, J=6.6 Hz), 1.40–1.59(3H, m), 2.96(1H, sext, J=6.6 Hz), 3.99(3H, s), 7.20–7.31(3H, m), 7.57(1H, brs), 7.64–7.68(1H, m), 8.04(1H, s)

(2) Process (b)

Preparation and catalytic reduction of a mixture of N-[2-(4-methyl-1-pentene-2-yl)phenyl-]-3-trifluoromethyl-1-methylpyrazole-4-carboxamide and N-[2-(1,3-dimethyl-1-butenyl)phenyl]-3-trifluoromethyl-1-methylpyrazole-4-carboxamide.

The same procedures as described in Example 2(1) were carried out except that 2-(1,3-dimethylbutyl)aniline was replaced by a 1:1 mixture of 2-(4-methyl-1-pentene-2-yl) aniline and 2-(1,3-dimethyl-1-butenyl) aniline. A mixture of N-[2-(4-methyl-1-pentene-2-yl)phenyl]-3-trifluoromethyl-1-methylpyrazole-4-carboxamide and N-[2-(1,3-dimethyl-1-butenyl)phenyl]-3-trifluoromethyl-1-methylpyrazole-4-carboxamide was obtained as a yellow crystal. Yield was 68%. Melting point was 66–74 ° C.

$^1$NMR(270 MHz, CDCl$_3$, δ ppm):0.86–1.01(6H,m), 1.58–1.67(0.5H, m), 1.93(1.5H, s), 2.20(1H, d, J=7.3 Hz), 2.62–2.76(0.5H, m), 3.99(3H, s), 5.09(0.5H, d, J=1.5 Hz). 5.28(0.5H, d, J=8.1 Hz), 5.34(0.5H, s), 7.11–7.13(2H, m), 7.24–7.33(1H, m), 7.91–8.02(2H, m), 8.23–8.29(1H, m)

To the mixture thus obtained, 5% Pd/C catalyst (50% wet) was added and stirred in a hydrogen atmosphere at room temperature for 3 hours. Thus obtained N-[2-(1,3-dimethylbutyl)phenyl]-3-trifluoromethyl-1-methylpyrazole-4-carboxamide was a colorless crystal. Yield was 70%.

(3) Process (c)

Preparation and dechlorination of N-[4-chloro-2-(1,3-dimethylbutyl)phenyl]-3-trifluoromethyl-1-methylpyrazole-4-carboxamide To a solution containing 0.33 g (1.55 mmol) of 4-chloro-2-(1,3-dimethylbutyl)aniline in 3 ml of pyridine, 0.35 g (1.63 mmol) of 3-trifluoromethyl-1-methylpyrazole-4-carbonyl chloride was added dropwise with stirring at room temperature.

After stirring for 1 hour, the reaction mixture was poured into a 5% aqueous hydrochloric acid solution and extracted with ethyl acetate. The organic layer was washed successively with a 5% aqueous hydrochloric acid solution, saturated aqueous sodium hydrogen carbonate solution and saturated aqueous sodium chloride solution and dried over anhydrous sodium sulfate. The solvent was distilled off with an evaporator under reduced pressure and the residue was purified by silica gel column chromatography using a mixture: n-hexane/ethyl acetate=1:1 as an eluent, and crystallized from hexane to obtain a colorless crystal. Thus obtained N-[4-(chloro-2-(1,3-dimethylbutyl) phenyl]-3-trifluoromethyl-1-methylpyrazole-4-carboxamide was 0.41 g.

Yield was 68%. Melting point was 155.8–156.9° C.

$^1$NMR(270 MHz, CDCl$_3$, δ ppm):0.82–0.84(6H, m), 1.17 (3H, d, J=6.6), 1.40–1.57(3H, m), 2.94(1H, sext, J=6.6 Hz), 4.00(3H, s), 7.18–7.26(2H, m), 7.52(1H, brs), 7.67(1H, d, J=8.1 Hz), 8.02(1H, s)

After dissolving the chloro compound thus obtained in 20 ml of ethyl alcohol, 0.2 g of a 5% Pd/C catalyst (50% wet) and 0.3 g of sodium acetate were added and stirred in a hydrogen atmosphere at room temperature for 3 hours. The reaction mixture was filtered to remove the Pd/C catalyst. The solvent was distilled off from the filtrate under reduced pressure. The residue was mixed with a saturated aqueous sodium hydrogen carbonate solution and extracted with ethyl acetate. The organic layer was washed with a saturated aqueous sodium chloride solution and dried over anhydrous sodium sulfate. The solvent was distilled off under reduced pressure to obtain the desired product as a brown oil. Yield was 79%.

Example 3

Preparation of N-[2-(1,3-dimethylbutyl)phenyl]-3-difluoromethyl-1-methylpyrazole-4-carboxamide (Compound No. 2)

(1) Process (a): direct process

The entitled compound was obtained by carrying out the same procedures as described in Example 2(1) except that 3-trifluoromethyl-1-methylpyrazole-4-carbonyl chloride was replaced by 3-difluoromethyl-1-methylpyrazole-4-carbonyl chloride. Melting point was 106–108° C.

$^1$NMR(270 MHz, CDCl$_3$, δ ppm):0.81(6H, d, J=5.9 Hz), 1.16(3H, d, J=6.6 Hz), 1.39–1.61(3H, m), 3.01–3.09(1H, m), 3.92(3H, s), 6.89(1H, t, J=54.2 Hz), 7.19–7.31(3H, m), 7.66–7.70(1H, m), 7.96(1H, brs), 8.00(1H, s)

Example 4

Preparation of N-[2-(3-methylpentyl)phenyl]-3-trifluoromethyl-1-methylpyrazole-4-carboxamide (Compound No. 3)

(1) Process (a): direct process

The entitled compound was obtained by carrying out the same procedures as described in Example 2(1) except that 2-(1,3-dimethylbutyl)aniline was replaced by 2-(3-methylpentyl)aniline.

Melting point was 166–167° C.

$^1$NMR(270 MHz, CDCl$_3$, δ ppm):0.85(3H, t, J=7.3 Hz), 0.90(3H, d, J=7.3 Hz), 1.12–1.25(1H, m), 1.32–1.43(3H, m), 1.55–1.64(1H, m), 2.53–2.63(2H, m), 3.98(3H, s), 7.13–7.26(3H, m), 7.60(1H, brs), 7.82(1H, d, J=7.3), 8.03 (1H, s)

(2) Process (c)

Preparation and dechlorination of N-[4-chloro-2-(3-methylpentyl) phenyl]-3-trifluoromethyl-1-methylpyrazole-4-carboxamide N-[4-chloro-2-(3-methylpentyl)phenyl]-3-trifluoromethyl-1-methylpyrazole-4-carboxamide was prepared by carrying out the same procedures in Example 2(3), Process (c) except that 4-chloro-2-(1,3-dimethylbutyl) aniline was replaced by 4-chloro-2-(3-methylpentyl) aniline. Melting point was 106–107° C.

$^1$NMR(270 MHz, CDCl$_3$, δ ppm):0.89(3H, t, J=7.3 Hz), 0.91(3H, d, J=7.3 Hz), 1.16–1.21(1H, m), 1.33–1.39(3H, m), 1.52–1.59(1H, m), 2.51–2.56(2H, m), 4.00(3H, s), 7.18–7.22(2H, m), 7.55(1H, brs), 7.81(1H, d, J=8.1), 8.05 (1H, s)

The chloro compound thus obtained was catalytically reduced in the presence of a 5% Pd/C catalyst and sodium acetate by carrying out the same procedures as described in Example 2(3), Process (c) to prepare N-[2-(3-methylpentyl) phenyl]-3-trifluoromethyl-1-methylpyrazole-4-carboxamide. Melting point was 166–168° C.

Example 5

Preparation of N-[2-(1,3-dimethylbutyl)phenyl]-2-methyl-4-trifluoromethylthiazole-5-carboxamide (Compound No. 5)

(1) Process (a): direct process

The entitled compound was prepared as an yellow oil by carrying out the same procedures as described in Example 1 except that 2,4-dimethylthiazole-5-carbonyl chloride was replaced by 2-methyl-4-trifluoromethylthiazole-5-carbonyl chloride.

$^1$NMR(270 MHz, CDCl$_3$, δ ppm):0.83(6H, d, J=5.9 Hz), 1.18(3H, d, J=7.3 Hz), 1.40–1.58(3H, m), 2.77(3H,s), 2.91 (1H, m), 7.23–7.32(3H, m), 7.62(1H, s), 7.67(1H, m)

Example 6

Preparation of N-[2-(1,3-dimethylbutyl)phenyl]-2-methyl-4-difluoromethylthiazole-5-carboxamide (Compound No. 6)

(1) Process (a): direct process

The entitled compound was prepared as an yellow oil by carrying out the same procedures as described in Example 1 except that 2,4-dimethylthiazole-5-carbonyl chloride was replaced by 2-methyl-4-difluoromethylthiazole-5-carbonyl chloride.

$^1$NMR(270 MHz, CDCl$_3$, δ ppm):0.83(6H, d, J=5.9 Hz), 1.19(3H, d, J=6.6 Hz), 1.40–1.59(3H, m), 2.77(3H, s), 2.94–3.01(1H, m), 7.03–7.43(4H, m), 7.67–7.72(2H, m)

Example 7

Preparation of N-[2-(3-methylbutyl)phenyl]-3-trifluoromethyl-1-methylpyrazole-4-carboxamide (Compound No. 4)

(1) Process (a): direct process

The entitled compound was prepared as a pale yellow crystal by carrying out the same procedures as described in Example 2(1) except that 2-(1,3-dimethylbutyl)aniline was replaced by 2-(3-methylbutyl)aniline.

Yield was 88%. Melting point was 128–129° C.

$^1$NMR(270 MHz, CDCl$_3$, δ ppm):0.92(6H, d, J=6.6 Hz), 1.42–1.48(2H, m), 1.55–1.64(1H, m), 2.56–2.62(2H, m), 3.99(3H, s), 7.16–7.27(3H, m), 7.60(1H, brs), 7.83(1H, d, J=8.1 Hz), 8.04(1H, s)

Preparation process of the sabstituted aniline intermediates will be illustrated hereinafter.

Example 8

Preparation of 2-(1,3-dimethylbutyl)aniline (B is methyl in the reaction formula 5)

(1) 2-(1-Hydroxy-1,3-dimethylbutyl)aniline

After dissolving 44.4 mmol of isobutylmagnesium bromide (2M ether solution) in 30 ml of a solvent mixture: ether/THF=1:1, a solution containing 2.0 g (14.8 mmol) of 2-aminoacetophenone in 10 ml of THF was added dropwise while maintaining the internal temperature at 15° C. or less. After stirring at 15° C. for an hour, the reaction mixture was poured into a saturated aqueous ammonium chloride solution and extracted with ethyl acetate. The organic layer was dried over anhydrous sodium sulfate. The solvent was distilled off under reduced pressure to obtain 2.9 g of the desired product as an yellow oil. Yield was quantitative.

$^1$NMR(270 MHz, CDCl$_3$, δ ppm):0.75(3H, d, J=6.6 Hz), 0.98(3H, d, J=6.6 Hz), 1.42–1.98(7H, m), 6.58–6.70(2H, m), 6.98–7.09(2H, m)

(2) A mixture of 2-(4-methyl-1-pentene-2-yl)aniline and 2-(1,3-dimethyl-1-butenyl)aniline After dissolving 0.55 g (2.85 mmol) of the above obtained 2-(1-hydroxy-1,3-dimethylbutyl)aniline in 20-ml of toluene, 0.05 g of p-toluenesulfonic acid monohydrate was added. A Dean-Stark separator was mounted on the reaction vessel and an azeotropic dehydration was carried out under reflux for 3 hours. The reaction mixture was mixed with ethyl acetate, washed with a saturated aqueous sodium hydrogen carbonate solution and dried over anhydrous sodium sulfate. The solvent was distilled off under reduced pressure and the residue was purified by silica gel column chromatography to obtain 0.43 g of the desired 1:1 mixture as an yellow oil. Yield was 86%.

$^1$NMR(270 MHz, CDCl$_3$, δ ppm):0.86–1.05(6H, m), 1.60 (0.5H, sept, J=6.6 Hz), 1.91–1.95(1.5H, m), 2.28(1H, d, J=6.6 Hz), 2.63–2.76(0.5H, m), 3.64(2H, brs), 5.10(0.5H, d, J=1.5 Hz), 5.24–5.33(1H, m), 6.67–6.75(2H, m), 6.96–7.08 (2H, m)

(3) 2-(1,3-dimethylbutyl)aniline

After dissolving 0.43 g (2.5 mmol) of the above obtained mixture in 10 ml of methanol, 0.2 g of 5% Pd/C catalyst (50% wet) was added, and stirred in a hydrogen atmosphere at room temperature for 7 hours. The reaction mixture was filtered to remove the catalyst. The solvent was distilled off from the filtrate under reduced pressure and the residue was dissolved in ethyl acetate, washed successively with a saturated aqueous sodium hydrogen carbonate solution and a saturated aqueous sodium chloride solution, and dried over anhydrous sodium sulfate. The solvent was distilled off under reduced pressure to obtain 0.40 g of the desired product as a brown oil. Yield was 91%.

$^1$NMR(270 MHz, CDCl$_3$, δ ppm):0.88–0.93(6H, m), 1.21 (3H, d, J=6.6 Hz), 1.36–1.44(1H, m), 1.51–1.66(2H, m), 2.85(1H, sext, J=6.6 Hz), 3.64(2H, brs), 6.66–6.80(2H, m), 6.98–7.10(2H, m)

Example 9

Preparation of 2-(3-methylpentyl)aniline (Process according to the reaction formula 6)

(1) 4-Chloro-2-(3-methylpentyl)nitrobenzene

After suspending 0.66 g (27.5 mmol) of magnesium in 10 ml of diethyl ether, a catalytic amount of iodine was added and 5.0 g (30.3 mmol) of 3-methylpentyl bromide was added dropwise under reflux. The mixture was stirred at room temperature for 30 minutes to obtain Solution A.

Separately, a solution containing 2.2 g (13.8 m mol) of p-chloronitrobenzene in 40 ml of tetrahydrofuran was prepared and Solution A obtained above was added dropwise while maintaining the temperature of the reaction mixture at −10° C. or less. After stirring at −10° C. for 20 minutes, a solution containing 1.5 g (9.66 mmol) of KMnO$_4$ in a mixture of 5 ml of acetone and 2 ml of water was added dropwise while maintaining the temperature of the reaction mixture at −20° C. or less. After stirring at −10° C. for 5 minutes, the reaction mass was poured into a saturated aqueous ammonium sulfate solution and filtered with Celite. The filtrate was extracted with ethyl acetate, washed with a saturated aqueous sodium chloride solution and dried over anhydrous sodium sulfate. The solvent was distilled off under reduced pressure. The residue was purified by silica gel column chromatography using a mixture: hexane/toluene=20:1 as an eluent to obtain 1.26 g of the desired product as an yellow oil. Yield was 38%.

$^1$NMR(270 MHz, CDCl$_3$, δ ppm):0.87(3H, t, J=7.3 Hz), 1.00(3H, d, J=7.3 Hz), 1.16–1.68(5H, m), 2.81–2.92(2H, m), 7.28–7.34(2H, m), 7.86(1H, d, J=8.1 Hz)

(2) 2-(3-Methylpentyl)aniline

After dissolving 0.8 g (3.31 mmol) of the above obtained nitro compound in 20 ml of ethyl alcohol, 0.2 g of a 5% Pd/C catalyst (50% wet) and 0.3 g (3.64 mmol) of sodium acetate were added and stirred in a hydrogen atmosphere at room temperature for 3 hours. The reaction mass was filtered to remove the Pd/C catalyst, and the solvent was distilled off from the filtrate under reduced pressure. The residue was mixed with a saturated aqueous sodium hydrogen carbonate solution and extracted with ethyl acetate. The organic layer was washed with a saturated aqueous sodium chloride solution, dried over anhydrous sodium sulfate. The solvent was distilled off under reduced pressure to obtain 0.54 g of the desired product as a brown oil. Yield was 79%.

$^1$NMR(270 MHz, CDCl$_3$, δ ppm):0.89(3H, t, J=7.3 Hz), 0.95(3H, d, J=7.3 Hz), 1.16–1.29(1H, m), 1.32–1.49(2H, m), 1.57–1.68(2H, m), 2.38–2.58(2H, m), 3.60(2H, brs), 6.66–6.76(2H, m), 6.99–7.06(2H, m)

Example 10

Preparation of 2-(1,3-dimethylbutyl)aniline (Process according to the reaction formula 6)

(1) 4-Chloro-2-(1,3-dimethylbutyl)nitorobenzne

The desired nitro compound was prepared by carrying out the same procedures as described in Example 9(1) except that 3-methylpentyl bromide was replaced by 1,3-dimethylbutyl bromide. Yield was 24%.

$^1$NMR(270 MHz, CDCl$_3$, δ ppm):0.84–0.88(6H, m), 1.25 (3H, d, J=7.3 Hz), 1.39–1.59(3H, m), 3.35(1H, sext, J=7.3 Hz), 7.25–7.33(1H, m), 7.39(1H, d, J=2.2 Hz), 7.65(1H, d, J=8.8 Hz)

(2) 2-(1,3-Dimethylbutyl)aniline

The desired compound was prepared by carrying out the same procedures as described in Example 9(2) except that 4-chloro-2-(3-methylpentyl)nitrobenzene was replaced by 4-chloro-2-(1,3-dimethylbutyl)nitrobenzene.

(3) 4-Chloro-2-(1,3-dimethylbutyl)aniline

To a mixture compound of 5 ml of ethanol and 0.95 g (3.93 mmol) of the nitro compound obtained in the Example 10(1), 5 ml of a 35% aqueous hydrogen chloride solution was added, and successively 3.1 g (16.56 mmol) of stannous chloride was added and heated at 60–70° C. for 1 hour. The reaction mass was poured into water, neutralized with sodium hydrogen carbonate, incorporated with Celite, and filtered. The filtrate was extracted with ethyl acetate. The organic layer was washed with a saturated aqueous sodium chloride solution and dried over magnesium sulfate. The solution was concentrated under reduced pressure by using an evaporator and purified by silica gel column chromatography using a mixture: hexane/ethyl acetate=10:1 as an eluent to obtain 0.74 g of the desired product as an yellow oil. Yield was 89%.

$^1$NMR(270 MHz, CDCl$_{3, δ\ ppm}$):0.88–0.93(6H, m), 1.18 (3H, d, J=7.3 Hz), 1.32–1.65(3H, m), 2.76(1H, sext, J=7.3 Hz), 3.61(2H, brs), 6.59(1H, d, J=8.8 Hz), 6.94–6.97(1H, m), 7.05(1H, d, J=2.2 Hz)

Example 11

Preparation of 2-(3-methylbutyl)aniline (Process according to the reaction formula 9)

(1) 2-(3-methylbutyl)nitrobenzene

After cooling 6 ml of concentrated sulfuric acid to 0° C., 4.3 g (29 mmol) of (3-methylbutyl)benzene was added dropwise and successively a mixture of 2 ml of concentrated sulfuric acid and 2 ml of concentrated nitric acid was added dropwise while maintaining the temperature of the reaction mass at 15° C. or less. After stirring at 0° C. for an hour, the reaction mixture was poured into water and extracted with ether. The organic layer was washed with a saturated aqueous sodium chloride solution and dried over anhydrous sodium sulfate. The solvent was distilled off under reduced pressure and the residue was purified by silica gel column chromatography using a mixture: hexane/toluene=20:1 as an eluent to obtain the desired two compound as an yellow oil. 2-(3-Methylbutyl)nitrobenzene was 0.63 g (27% yield) and 4-(3-methylbutyl)nitrobenzene was 0.9 g (36% yield). Physical properties of 2-(3-methylbutyl)nitrobenzene $^1$NMR(270 MHz, CDCl$_3$, δ ppm):0.95(6H, d, J=6.6 Hz), 1.47–1.56(2H, m), 1.65(1H, sept, J=6.6 Hz), 2.84–2.90(2H, m), 7.29–7.36(2H, m), 7.50(1H, t, J=8.1 Hz), 7.87(1H, t, J=8.1 Hz)

(2) 2-(3-methylbutyl)aniline

To a mixture composed of 10 ml of methanol, 1.3 g (6.4 mmol) of the above 2-(3-methylbutyl)nitrobenzene, and 6.4 ml of concentrated aqueous hydrochloric acid solution, 1.4 g (25.1 mmol) of reduced iron was added in portions and heated to 60° C. with stirring for 1 hour. The reaction mass was poured into water, neutralized with a saturated aqueous sodium hydrogen carbonate solution and filtered to remove precipitated iron hydroxide. The filtrate was extracted with ethyl acetate, washed with a saturated aqueous sodium chloride solution and dried over anhydrous sodium sulfate. The solvent was distilled off under reduced pressure to obtain 0.95 g of the desired product as oil. Yield was 85%.

$^1$NMR(270 MHz, CDCl$_3$, δ ppm):0.96(6H, d, J=6.6 Hz), 1.45–1.54(2H, m), 1.63(1H, sept, J=6.6 Hz), 2.45–2.51(2H, m), 3.59(2H, brs), 6.66–6.76(2H, m), 6.99–7.06(2H, m)

Formulation examples and test examples of the plant disease control agent will be illustrated hereinafter.

Formulation Example 1 (Dust)

A dust containing 2% by weight of an active ingredient was obtained by uniformly mixing and grinding 2 parts by weight of the compound having Compound No. 1, 98 parts by weight of clay.

Formulation Example 2 (Wettable Powder)

A wettable powder which had a uniform composition, was a pulverized particle, and contained 10% by weight of an active ingredient was obtained by uniformly mixing and grinding 10 parts by weight of the compound having Compound No. 2, 70 parts by weight of kaolin, 18 parts by weight of white carbon and 2 parts by weight of calcium alkylbenzenesulfonate.

Formulation Example 3 (Wettable Powder)

A wettable powder which had a uniform composition, was a pulverized particle, and contained 20% by weight of an active ingredient was obtained by uniformly mixing 20 parts by weight of the compound having Compound No. 3, 3 parts by weight of calcium alkylbenzenesulfonate, 5 parts by weight of polyoxyethylene nonyl phenyl ether and 72 parts by weight of clay.

Formulation Example 4 (Wettable Powder)

A wettable powder containing 50% by weight of an active ingredient was obtained by uniformly mixing and grinding 50 parts by weight of the compound having Compound No. 5, 1 part by weight of sodium lignin sulfonate, 5 parts by weight of white carbon and 44 parts by weight of diatomaceous earth.

Formulation Example 5 (Flowable Formulation)

A flowable formulation containing 5% by weight of an active ingredient was obtained by wet grinding with a sand grinder 5 parts by weight of the compound having Compound No. 6, 7 parts by weight of propylene glycol, 4 parts by weight of sodium lignin sulfonate, 2 parts by weight of sodium dioctylsulfosuccinate and 82 parts by weight of water.

Formulation Example 6 (Flowable Formulation)

A flowable formulation containing 10% by weight of an active ingredient was prepared by wet grinding with a sand grinder 10 parts by weight of the compound having Compound No. 7, 7 parts by weight of propylene glycol, 2 parts by weight of sodium lignin sulfonate, 2 parts by weight of sodium dioctylsulfosuccinate, and 79 parts by weight of water.

Formulation Example 7 (Flowable Formulation)

A flowable formulation containing 25% by weight of an active ingredient was obtained by wet grinding with a sand grinder 25 parts by weight of the compound having Compound No. 2, 5 parts by weight of propylene glycol, 5 parts by weight of polyoxyethyleneoleate ester, 5 parts by weight of polyoxyethylene diallyl ether sulfate, 0.2 part by weight of silicone-based antifoaming agent and 59.8 parts by weight of water.

Text Example 1

Control test on *Pyricularia oryzae* of rice plant

In a green house, 40–50 seedlings of rice plant (breed: Mangetsumochi) were grown in each pot until the two leaf stage. A wettable powder which was prepared according to Formulation Example 3 was diluted to the prescribed concentration (active ingredient concentration of 50 ppm) and sprayed on the seedlings by 50 ml portions per three pots.

After the spray chemical was dried, a conidiospore suspension (4×10$^5$ spores/ml) was prepared from *Pyricularia oryzae* which was cultured on an oatmeal medium and spray-inoculated over the whole surface of seedlings. Thus treated seedlings were allowed to stay in a plant growth chamber at temperature of 25° C. under relative humidity of 95% or more for 8 days.

After 8 days from the inoculation, the lesion number of *Pyricularia oryzae* per five seedlings of rice plant was assessed on the basis of the following index and a control value was obtained according to the described formula. Results are illustrated in Table 1

Severity

0: no lesion
1: 1–2 lesions
2: 3–5 lesions
3: 6–10 lesions
4: 11 or more lesions The mean value of each treated area and untreated area is defined as severity.

Control value (%)=(1-severity in the treated area/severity in the untreated area)×100

Test Example 2

Control test on *Botrytis cinerea* of kidney beans

In a green house, two seedlings of kidney beans (cultivar: Vineless top crop) were grown in each plastic pot having a diameter of 7.5 cm until development of cotyledon.

A wettable powder which was prepared according to Formulation Example 3 was diluted to the prescribed concentration (active ingredient concentration of 50 ppm) and sprayed by 50 ml portions per three pots.

After the sprayed chemical was dried, a conidiospore suspension (1×10$^6$ spores/ml) was prepared from *Botrytis cinerea*(MBC resistant, RS strain) which was previously cultured on a PDA medium was spray-inoculated on the cotyledon and allowed to stay in the plant growth chamber at temperature of 20–23° C., under relative humidity of 95% or more for 7 days.

After 7 from the inoculation, the lesion area of *Botrytis cinerea* per leaf of kidney beans was assessed on the basis of the following index. The grade of severity is shown by the index and the cotrol value was calculated by the formula below. Results are shown in Table 1

Severity

0: no lesion
1: lesion area was 5% or less
2: lesion area was 5–25%
3: lesion area was 25–50%
4: lesion area was 50% or more The mean value of each treated area and untreated area was defined as severity.

Control value (%)=(1-severity in the treated area/severity in the untreated area)×100

Test Example 3

Control test on *Sphaerotheca fuliginea* of cucumber

In a green house, two seedlings of cucumber (cultivar: Sagami semi-white) were grown in each pot having a diameter of 7.5 cm until the 1.5 leaf stage.

A wettable powder which was prepared according to Formulation Example 3 was diluted to the prescribed concentration (active ingredient concentration of 25 ppm) and sprayed on the seedlings by 50 ml portions per three pots and dried in the air.

A conidiospore suspension (1×10⁶ spore/ml) was prepared by suspending conidiospore of cucumber *Sphaerotheca fuliginea* in water which contained a small amount of spreader, and spray-inoculated on the seedlings and allow to stay in the plant growth chamber for 7 days.

After 7 days from the inoculation, the lesion area of *Sphaerotheca fuliginea* per leaf of cucumber was assessed on the basis of the index described in Test Example 2. The grade of the severity is shown by the index and control value was calculated by the formula below. Results are illustrated in Table 1.

Control value (%)=(1-in the treated area/severity in the untreated area)×100

TABLE 1

| Compound No. | Control value | | |
|---|---|---|---|
| | *Pyricularia oryzae* | *Botrytis cinerea* | *Sphaerotheca fuliginea* |
| 1 | 100 | 100 | 100 |
| 2 | 100 | 100 | 100 |
| 3 | 100 | 100 | 100 |
| 4 | 100 | 100 | 100 |
| 5 | 100 | 100 | 100 |
| 6 | 100 | 100 | 100 |
| 7 | 100 | 95 | 95 |
| Ref. Compound 1 | 100 | — | — |
| Ref. Compound 2 | — | 100 | — |
| Ref. Compound 3 | — | — | 100 |
| Ref. Compound 4 | 0 | 40 | 0 |
| Ref. Compound 5 | 0 | 70 | 20 |
| Ref. Compound 6 | 0 | 15 | 0 |
| Ref. Compound 7 | 0 | 80 | 20 |
| Ref. Compound 8 | 0 | 0 | 0 |
| Ref. Compound 9 | 0 | 0 | 0 |
| Ref. Compound 10 | 0 | 0 | 0 |
| Ref. Compound 11 | 0 | 0 | 0 |
| Ref. Compound 12 | 0 | 0 | 0 |
| Ref. Compound 13 | 0 | 0 | 0 |
| Ref. Compound 14 | 0 | 0 | 0 |

Reference Compounds 1–3 are marketed compounds. Reference Compounds 5, 7 and 13 are described in the examples of European Patent A-589301. Reference Compounds 4, 6 and 8 are described in the tables of the same patent. Reference Compounds 9–12 are involved in the next higher concept of the above gazette, although not exemplified. Reference Compound 14 is described in the example of European Patent A-545099.

Specific compounds are described below.

Reference Compound 1: tricyclazol(5-methyl-1,2,4-triazolo[3,4-b]benzothiazole

Reference Compound 2: procymidone[(N-(3,5-dichlorophenyl)-1,2-dimethylcyclopropane-1,2-dicarboximide]

Reference Compound 3: triadimefon[(1-(4-chlorophenoxy)-3,3-dimethyl-1-(1,2,4-triazol-1-yl)-2-butanone)]

Reference Compounds 4–12 are represented by the formula (15) and R is a group shown below.

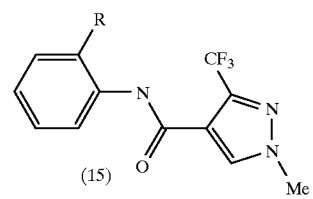

Reference Compound 4: R is 1-methylethyl.
Melting point is 115–117° C.
Reference Compound 5: R is 1-methylpropyl.
Melting point is 137–138° C.
Reference Compound 6: R is tert-butyl.
Oil.
Reference Compound 7: R is 2-ethylbutyl.
Melting point is 84–87° C.
Reference Compound 8: R is 1-methylhexyl.
Melting point is 119.5–120.50° C.
Reference Compound 9: R is 1,4-dimethylpentyl.
Melting point is 109–110° C.
Reference Compound 10: R is 1-ethyl-3-methylbutyl.
Melting point is 121–123° C.
Reference Compound 11: R is 1,3-dimethylhexyl.
Melting point is 84–86° C.
Reference Compound 12: R is 2,6-dimethylbutane-4-yl.
Melting point is 70–72° C.

Reference Compounds 13 and 14 are following compounds.

Reference Compound 13: N-[2-(1-methylpropyl)phenyl]-1,3-dimethylpyrazole-4-carboxamide (melting point: 154–156° C.)

Reference Compound 14: N-[2-(1-methylethyl)phenyl]-2-methyl-4-trifluoromethylthiazole-5-carboxamide (melting point: 114–115° C.)

Test Example 4

Control test on *Pucciia recondita* of wheat

In a green house, 15–20 seedlings of wheat (cultivar: Norin No. 61) were grown in each plastic pot having a diameter of 6 cm until the 1.5 leaf stage. A wettable powder which was prepared from the compound of the invention according to Formulation Example 3 was diluted to the prescribed concentration (active ingredient concentration of 25 ppm) and sprayed on the seedlings by 50 ml portions per three pots.

After the sprayed chemical was dried, an uredospore of *Pucciia recondita* of wheat was spray-inoculated and allowed to stay in a humidified condition for 2 days and then transferred to a room maintained at 18° C.

After 10 days from the inoculation, the lesion area on the first leaf of wheat was assessed. Results are shown in Table 2. The severity and control value were obtained by the same method as Test Example 2.

TABLE 2

| Compound No. | Control Value (%) |
|---|---|
| 1 | 100 |
| 2 | 100 |
| 3 | 100 |
| 4 | 100 |
| 5 | 100 |
| 6 | 100 |
| 7 | 100 |

Test Example 5

Control on *Rhizoctonia solani* of rice plant

In a green house, 5 pairs of seedlings of rice plant (cultivar: Tsukimimochi) were grown until the tillering stage at planting of two seedlings per spot in a color pot having on area of 1/10,000a.

A wettable powder which was prepared from the compound of the invention according to Formulation Example 3 was diluted to the prescribed concentration (active ingredient concentration of 200 ppm) and sprayed on the seedlings by 100 ml portions per three pots.

After the sprayed chemical was dried, *Rhizoctonia solani* of rice plant was previously cultured on a PDA medium and the PDA medium was cut with a cork borer. The fungus cell thus obtained was inoculated in the leaf sheath at 5 spots per pot and transferred into a plant growth chamber maintained at temperature of 25° C. and humidity of 95% or more to stimulate disease development. Examination was carried out by confirming disease development in the untreated area and measuring the length of lesion. Severity was examined on the basis of the following index. Control value was calculated by same method as Test Example 1. The grade of severity is shown below. Results are illustrated in Table 3.

Severity

0: no lesion
1: lesion length was 5% or less
2: lesion length was 5–25%
3: lesion length was 25–50%
4: lesion length was 50% or more The mean value of each treated area and untreated area was defined as severity.

TABLE 3

| Compound No. | Control value (%) |
|---|---|
| 1 | 100 |
| 2 | 100 |
| 3 | 100 |
| 4 | 100 |
| 5 | 100 |
| 6 | 100 |
| 7 | 100 |

Test Example 6

Pot test on *Alternaria mali* of apple

Three tests were conducted simultaneously.

A wettable powder which was prepared from the compound of the invention according to Formulation Example 3 was diluted to the prescribed concentration (active ingredient concentration of 50 ppm) and spray-applied to three shoots of apple (cultivar: Star King) which was soon after development and had unhardened leaves with an automatic spraying machine in an amount of 50 ml. The sprayed chemical was dried in the air. Neosterin was added as a spreader so as to obtain a 3000 times dilution.

A conidiospore of *Alternaria mali* of apple which was previously obtained by culturing on PDA medium at 28° C. for 10 days was suspended in distilled water containing Tween 20 so as to obtain a dilution of 5000 times, washed once by centrifugal treatment, and suspended again in Tween 20 containing distilled water so as to obtain a spore concentration of $1 \times 10^5$ spore/ml. The suspension thus obtained was spray-inoculated in an amount around 2 ml per one shoot.

After maintaining in an inoculation box at 28° C. for 7 days, lesion area on 6–9 completely developed leaves per one turion was examined. Judgment of severity and calculation of control value were carried out by the same method as Test Example 2. Results are illustrated in Table 4.

TABLE 4

| Compound No. | Lesion area | Control value (%) |
|---|---|---|
| 1 | 10.8 | 84 |
| 2 | 15.3 | 78 |
| untreated | 68 | — |

Test Example 7

Control test on *Gymnosporangium haraeanum* of pear

Three tests were conducted simultaneously. At the end of foliation stage (April 24), to 2–5 year grown and direct-planted young trees of pear (cultivar: Kosui), a wettable powder which was prepared from the compound of the invention according to Formulation Example 3 was diluted to the prescribed concentration (active ingredient concentration of 50 ppm), incorporated with Neosterin as a spreader so as to obtain a dilution of 5000 times and sufficiently sprayed with a small type sprayer.

*Gymnosporangium haraeanum* of pear was allowed to spontaneous development. After 2 weeks, the number of lesion was assessed. Only orange lesions were counted and curative lesions were excluded.

The relationship between leaf development of pear and formation of lesions were as follows.

April 15: Foliation stage. Early foliated leaves have slight lesion.

April 25: End of foliation stage. Small lesions were found.

Judgment of severity and calculation of control value were carried out by the same method as Test Example 1. Results are illustrated in Table 5.

TABLE 5

| Compound No. | Lesions (number/leaf) | Control value (%) |
|---|---|---|
| 1 | 0.0 | 100 |
| 5 | 0.2 | 99.6 |
| 7 | 2.3 | 95.2 |
| Untreated | 48.3 | |

Test Example 8

Control test on *Venturia inaequalis* of apple

Three test were conducted simultaneously. Apple seedlings in 3–4 leaf stage (cultivar: Kogyoku) were transplanted to a plastic pot which had a diameter of 6 cm. A wettable powder which was prepared from the compound of the invention according to Formulation Example 3 was diluted to the prescribed concentration (active ingredient concentration of 50 ppm), incorporated with Neosterin as a spreader so as to obtain a dilution of 3000 times, and sprayed with an automatic spraying machine in amount of 30 ml for per three pots. The sprayed chemical was air-dried.

The conidiospore of *Venturia inaequalis* which was formed on the diseased leaves of apple was suspended in a sterilized water, preserved in the stage of freezing, thawed prior to use, and prepared so as to obtain a concentration of $5 \times 10^5$ spore/ml. Spray inoculation was carried out with a chromatosprayer after 24 hours from spraying of the chemical. After storing in an inoculation box at 18° C. for 48 hours, the apple seedlings were maintained at 22° C. for 11 days in a cell which was installed in the green house. After 13 days from the inoculation, upper two leaves were assessed on the basis of the following standard. Results are illustrated in Table 6.

Severity index
0: no lesion
1: slight lesion (lesion can be slightly found)
2: light lesion (lesion can be found)
3: medium (lesion is remarkable)
4: heavy (leaves were deformed by lesion)
5: severe (portionally died by lesion)
Severity is mean value of each treated and untreated area.
Severity=Σ(index×the number of diseased leaves)×100/(5×total leaves assessed)
Control value (%)=(1-severity of treated area/severity of untreated area)×100

TABLE 6

| Compound No. | Lesion (number/leaf) | Control value (%) |
|---|---|---|
| 1 | 0.0 | 100 |
| 2 | 0.0 | 100 |
| Untreated | 8.0 | — |

Test Example 9

Test on residual activity against *Botrytis cinerea* of kidney beans

In a green house, three seedlings of kidney beans (cultivar: Veinless top crop) were grown until development of cotyledon in each plastic pot having a diameter of 7.5 cm.

A wettable powder which was prepared according to Formulation Example 3 was diluted to a prescribed concentration (active ingredient concentration of 62.5 ppm) and sprayed by 80 ml portions per three pots. After the prescribed days from spraying, one cotyledon was individually cut from each pot.

A conidiospore suspension ($1 \times 10^6$ spore/ml) was prepared from *Botrytis cinerea* (MBC resistant, RS strain) which was previously cultured on a PDA medium and absorbed on a paper disc having a diameter of 8 mm. Inoculation was carried out by placing the absorbed paper disk on the above cotyledon. After allowing to stay at 20° C. under humidity of 95% or more for 4 days, the area of lesion was measured. Judgment of severity was carried out by the same method as Test Example 2. Control value was calculated from the results obtained according to the below described formula. Results are illustrated in Table 7.

Control value (%)=(1-severity of treated area/severity of untreated area)×100

TABLE 7

| | Control value (%) | | |
|---|---|---|---|
| Compound No. | 5 days | 8 days | 12 days |
| 1 | 100 | 100 | 100 |
| Ref. Compound 1 | 66 | 34 | 10 |
| Ref. Compound 7 | 75 | 52 | 25 |
| Untreated | 10.2 | 12.8 | 12.0 |

Test Example 10

Mycelia elongation inhibition test

The compounds having Compound No. 1 and Compound No. 7 were diluted to an active ingredient concentration of 50 ppm and three tests were simultaneously conducted by way of an agar disk dilution method using PDA medium. Final acetone concentration was made 2%. The fungi were inoculated by using a colony disk inoculation method and cultured at 25° C. for 4 days. The diameter of untreated colony was measured and indicated as $R_0$. The diameter of colony treated with each compound was measured and indicated as $R_1$. A mycelia elongation inhibition rate (%) was calculated from the following formula on the basis of measured values. Results are illustrated in Table 8.

Abbreviations in the table indicate following fungi.
C.A.: *Cercospora arachidicola* of peanut
R.S.: *Rhizoctonia solani* of cucumber
S.S.: *Sclerotinia sclerotiorum* of beans
A.K.: *Alternaria kikuchiana* of pear
Mycelia elongation inhibition rate (%)=$(R_0-R_1)/R_0 \times 100$

TABLE 8

| Compound No. | C.A. | R.S. | S.S. | A.K. |
|---|---|---|---|---|
| 1 | 90 | 93 | 90 | 90 |
| 7 | 90 | 95 | 90 | 94 |

Test Example 11

Spore germination inhibition test (Cellophane method)

The compounds having Compound No. 1 and Compound No. 7 were diluted to an active ingredient concentration of 50 ppm. An eight folded gauze was placed in a Petri dish and 20 ml of the chemical prepared above was permeated. Final acetone concentration was made 2%. The Petri dish was covered with cellophane. A suspension of fungus spore (spore density: $5 \times 10^5$ spore/ml) containing 5% of glucose was placed by 10 µl portions on each cellophane and cultured at 20° C. for 24 hours. Thereafter spore germination was observed under a microscope.

Three examinations were simultaneously carried out, and the grade of spore germination was ranked 0, 1 and 2. A case having the grade 2 was regarded as germination. Germination inhibition rate was calculated from the following formula wherein $R_0$ is a germination rate when culture was conducted in the absence of the chemical and $R_1$ is a germination rate when culture was conducted in the presence of the chemical. Results are illustrated in Table 9.

Abbreviations in the table indicate following fungi.

*M.N.: Mycovellosiella nattrassii* of eggplant

*P.G.: Fusarium graminearum* of wheat

*S.H.: Sphaerotheca humuli* of strawberry

*V.N.: Venturia nashicola* of pear

Grade of Germination

0: No germination was found

1: Elongation of a germination tube was less than the length of the spore.

2: Elongation of a germination tube was the length of the spore or more.

Germination inhibition rate (%)=$(R_0-R_1)/R_0 \times 100$

TABLE 9

| Compound No. | M.N. | F.G. | S.H. | V.N. |
|---|---|---|---|---|
| 1 | 100 | 93 | 100 | 95 |
| 7 | 100 | 90 | 100 | 100 |

Effect of the Invention

The substituted carboxamide derivative represented by the formula (1) in the invention exhibits by single formulation an excellent activity against rice blast of rice plant, gray mold, and powdery mildew of melons, and also exerts effect against rust, sheath blight of rice plant and other various diseases of plant, and thus has a very broad fungicidal spectrum. The derivative has excellent residual effect. Further, the derivative shows a control effect against gray mold at a lower dosage as compared with the prior art and is safe for crops. Consequently, the derivative is useful as a plant disease control agent.

What is claimed is:

1. A substituted carboxanilide derivative represented by the formula (1):

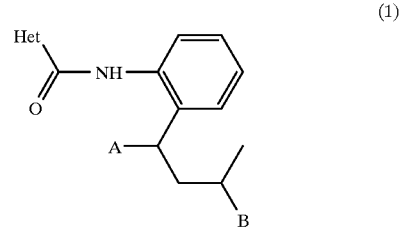

(1)

wherein A is methyl, B is a methyl, and Het is a heterocyclic group represented by H1:

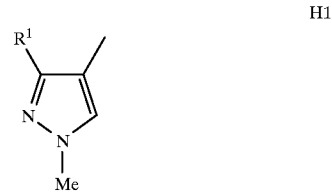

H1 wherein $R^1$ is a trifluoromethyl or difluoromethyl.

2. The substituted carboxamide derivative according to claim 1 wherein $R^1$ is a trifluoromethyl.

3. The plant disease control agent comprising the substituted carboxanilide derivative according to claim 1 as an active ingredient.

4. The plant disease control agent comprising the substituted carboxanilide derivative according to claim 2 as an active ingredient.

5. The agricultural and horticultural fungicide comprising the substituted carboxanilide derivative according to claim 1 as an active ingredient.

6. The agricultural and horticultural fungicide comprising the substituted carboxanilide derivative according to claim 2 as an active ingredient.

* * * * *